US00PP32614P2

(12) United States Plant Patent
Danziger

(10) Patent No.: US PP32,614 P2
(45) Date of Patent: Dec. 8, 2020

(54) ***PORTULACA* PLANT NAMED 'DPORMOJAFU'**

(50) Latin Name: *Portulaca umbraticola*
Varietal Denomination: DPORMOJAFU

(71) Applicant: Gavriel Danziger, Moshav Mishmar Hashiva (IL)

(72) Inventor: Gavriel Danziger, Moshav Mishmar Hashiva (IL)

(73) Assignee: DANEIGER "DAN" FLOWER FARM, Beit Dagan (IL)

( * ) Notice: Subject to any disclaimer, the term of this patent is extended or adjusted under 35 U.S.C. 154(b) by 0 days.

(21) Appl. No.: 16/873,551

(22) Filed: Apr. 30, 2020

(30) Foreign Application Priority Data

May 17, 2019 (CA) ..... PBR 19-9863

(51) Int. Cl.
*A01H 5/02* (2018.01)
*A01H 6/00* (2018.01)

(52) U.S. Cl.
USPC ..... Plt./471
CPC ..... *A01H 6/00* (2018.05)

(58) Field of Classification Search
USPC ..... Plt./471
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Portulaca* plant named 'DPORMOJAFU', characterized by its upright to outwardly spreading and mounding plant habit; vigorous growth habit and rapid growth rate; freely branching habit; early and freely flowering habit; large reddish purple-colored flowers; and good garden performance.

1 Drawing Sheet

Botanical designation: *Portulaca umbraticola.*
Cultivar denomination: 'DPORMOJAFU'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9863. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Portulaca* plant, botanically known as *Portulaca umbraticola* and hereinafter referred to by the name 'DPORMOJAFU'.

The new *Portulaca* plant is a product of a planned breeding program conducted by the Inventor in Nir-Zvi, Israel. The objective of the breeding program is to create new spreading *Portulaca* plants with numerous large and attractive flowers.

The new *Portulaca* plant originated from a self-pollination made by the Inventor in Nir-Zvi, Israel in June, 2013 of a proprietary selection of *Portulaca umbraticola* identified as code number PT-11-856, not patented. The new *Portulaca* plant was discovered and selected by the Inventor as a flowering plant from within the progeny of the stated self-pollination in a controlled greenhouse environment in Nir-Zvi, Israel on Sep. 7, 2014.

Asexual reproduction of the new *Portulaca* plant by vegetative terminal cuttings in a controlled greenhouse environment in Nir-Zvi, Israel since September, 2014, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DPORMOJAFU'. These characteristics in combination distinguish 'DPORMOJAFU' as a new and distinct *Portulaca* plant:

1. Upright to outwardly spreading and mounding plant habit.
2. Vigorous growth habit and rapid growth rate.
3. Freely branching habit.
4. Early and freely flowering habit.

5. Large reddish purple-colored flowers.
6. Good garden performance.

Plants of the new *Portulaca* can be compared to plants of the parent selection. Plants of the new *Portulaca* differ primarily from plants of the parent selection in the following characteristics:

1. Plants of the new *Portulaca* are more freely flowering than plants of the parent selection.
2. Flowers of plants of the new *Portulaca* are smoother than and not as rugose as flowers of plants of the parent selection.
3. Flowers of plants of the new *Portulaca* are reddish purple in color whereas flowers of plants of the parent selection are dark pink in color.

Plants of the new *Portulaca* also can be compared to plants of the *Portulaca oleracea* 'DPAZFCHSIA', disclosed in U.S. Plant Pat. No. 27,540. In side-by-side comparisons, plants of the new *Portulaca* differ primarily from plants of 'DPAZFCHSIA' in the following characteristics:

1. Plants of the new *Portulaca* are more vigorous than plants of 'DPAZFCHSIA'.
2. Plants of the new *Portulaca* are more freely branching than plants of 'DPAZFCHSIA'.
3. Plants of the new *Portulaca* are more freely flowering than plants of 'DPAZFCHSIA'.
4. Plants of the new *Portulaca* have larger flowers than plants of 'DPAZFCHSIA'.

Plants of the new *Portulaca* can also be compared to plants of the *Portulaca oleracea* 'Nano Fuchsia', not patented. In side-by-side comparisons, plants of the new *Portulaca* differ primarily from plants of 'Nano Fuchsia' in the following characteristics:

1. Plants of the new *Portulaca* are more vigorous and larger than plants of 'Nano Fuchsia'.
2. Plants of the new *Portulaca* have larger flowers than plants of 'Nano Fuchsia'.

BRIEF DESCRIPTION OF THE PHOTOGRAPHS

The accompanying colored photographs illustrate the overall appearance of the new *Portulaca* plant showing the colors as true as it is reasonably possible to obtain in colored reproductions of this type. Colors in the photographs may differ slightly from the color values cited in the detailed botanical description which accurately describe the colors of the new *Portulaca* plant.

At the top of the photographic sheet (FIG. 1) is a side perspective view of a typical flowering plant of 'DPORMOJAFU' grown in a container and at the bottom of the photographic sheet is a close-up view of a typical flowering plant of 'DPORMOJAFU'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Portulaca* production. During the production of the plants, day temperatures averaged 33° C. and night temperatures averaged 15° C. Plants were pinched three weeks after planting and were twelve weeks from planting rooted cuttings when the photographs and description were taken. In the following description, color references are made to The Royal Horticultural Society Colour Chart, 2007 Edition, except where general terms of ordinary dictionary significance are used.

Botanical classification: *Portulaca umbraticola* 'DPORMOJAFU'.

Parentage:

*Female, or seed, parent*.—Proprietary selection of *Portulaca umbraticola* identified as code number PT-11-856, not patented.

*Male or pollen parent*.—Proprietary selection of *Portulaca umbraticola* identified as code number PT-11-856, not patented.

Propagation:

*Type*.—By vegetative terminal cuttings.

*Time to initiate roots, summer*.—About eight to twelve days at temperatures about 16° C. to 20° C.

*Time to produce a rooted young plant, summer*.—About four weeks.

*Root description*.—Fine, fibrous; close to 155A in color, actual color of the roots is dependent on substrate composition, water quality, fertilizers, substrate temperature and age of roots.

*Rooting habit*.—Freely branching; dense.

Plant description:

*Plant and growth habit*.—Upright to outwardly spreading and mounding plant habit; vigorous growth habit and rapid growth rate.

*Branching habit*.—Freely branching habit about seven primary lateral branches each with about eight secondary lateral branches developing per plant; pinching enhances branching potential.

*Plant height*.—About 26.2 cm.

*Plant diameter* (*area of spread*).—About 60.9 cm.

Lateral branch/peduncle description:

*Length*.—About 24.2 cm.

*Diameter*.—About 2.5 mm.

*Internode length*.—About 2.9 cm.

*Strength*.—Moderately strong, flexible.

*Texture and luster*.—Smooth, glabrous; moderately glossy.

*Color, developing*.—Close to 145B.

*Color, developed*.—Close to 145C tinged with close to 182B to 182C.

Leaf description:

*Arrangement*.—Alternate, simple.

*Length*.—About 4.5 cm.

*Width*.—About 3.1 cm.

*Shape*.—Obovate.

*Apex*.—Broadly acute to obtuse.

*Base*.—Cuneate.

*Margin*.—Entire.

*Texture and luster, upper and lower surfaces*.—Smooth, glabrous; fleshy, succulent; somewhat glossy.

*Venation pattern*.—Pinnate.

*Color*.—Developing leaves, upper surface: Close to 137C. Developing leaves, lower surface: Close to 138B. Fully expanded leaves, upper surface: Close to 137C to 137D; along the margins, close to N186C; venation, close to 147C to 147D. Fully expanded leaves, lower surface: Close to 138B; venation, close to 144A.

*Petioles*.—Length: About 4.9 mm. Diameter: About 2.5 mm. Texture and luster, upper and lower surfaces:

Smooth, glabrous; semi-glossy. Strength: Moderately strong. Color, upper and lower surfaces: Close to 144A.

Flower description:

*Flower arrangement*.—Single rotate flowers; freely flowering habit with 235 open flowers and flower buds per plant at one time; flowers face mostly upright to outwardly.

*Fragrance*.—None detected.

*Natural flowering season*.—Plants begin flowering about four weeks after planting; in the garden, plants flower continuously from spring until autumn in Southern Ontario, Canada.

*Flower longevity*.—Flowers last about one day on the plant; flowers not persistent.

*Flower buds*.—Length: About 1.4 cm. Diameter: About 6 mm. Shape: Ovoid. Texture and luster: Smooth, glabrous; slightly glossy. Color: Close to 145A to 145B.

*Flower diameter*.—About 3.8 cm.

*Flower length* (*height*).—About 1.3 cm.

*Petals*.—Quantity per flower: Corolla consists of five petals fused at the base. Length: About 2.3 cm. Width: About 2 cm. Shape: Obovate. Apex: Rounded or emarginate. Base: Fused, truncate. Margin: Entire, moderately undulate. Texture and luster, upper surface: Smooth, glabrous, satiny; slightly glossy. Texture and luster, lower surface: Smooth, glabrous; matte. Color: When opening, upper surface: Brighter than N74A. When opening, lower surface: Close to N74B. Fully opened, upper surface: Close to N74A; towards the base, close to 43A; at the base, close to 7A; venation, similar to lamina colors; main color becoming closer to N74B with development. Fully opened, lower surface: Close to N74B; towards the base, streaks, close to 75C to 75D; venation, similar to lamina colors; main color becoming closer to N74B with development.

*Sepals*.—Quantity per flower: Two fused into a tubular calyx. Length: About 8 mm. Width: About 7 mm. Shape: Ovate; somewhat concave. Apex: Acute. Base: Fused, acute. Margin: Entire. Texture and luster, upper and lower surfaces: Smooth, glabrous; slightly glossy. Color, upper and lower surfaces: Close to 145C.

*Reproductive organs*.—Androecium: Quantity of stamens per flower: About 58. Filament length: About 4 mm. Filament color: Close to 21B; distally, close to N34A. Anther shape: Oblong. Anther length: Less than 1 mm. Anther color: Close to 21A. Amount of pollen: Abundant. Pollen color: Close to 23A. Gynoecium: Pistil length: About 9 mm. Style length: About 4 mm. Style color: Close to 145A. Stigma diameter: About 6 mm. Stigma color: Close to 185B to 185C. Ovary color: Close to 145A. Fruits and seeds: To date, fruit and seed development have not been observed on plants of the new *Portulaca*.

Garden performance: Plants of the new *Portulaca* have been observed to have good garden performance and to tolerate temperatures ranging from about 7° C. to about 35° C. and to be suitable for USDA Hardiness Zone 11.

Pathogen & pest resistance: To date, plants of the new *Portulaca* have not been shown to be resistant to pathogens and pests common to *Portulaca* plants.

It is claimed:

1. A new and distinct *Portulaca* plant named 'DPORMOJAFU' as illustrated and described.

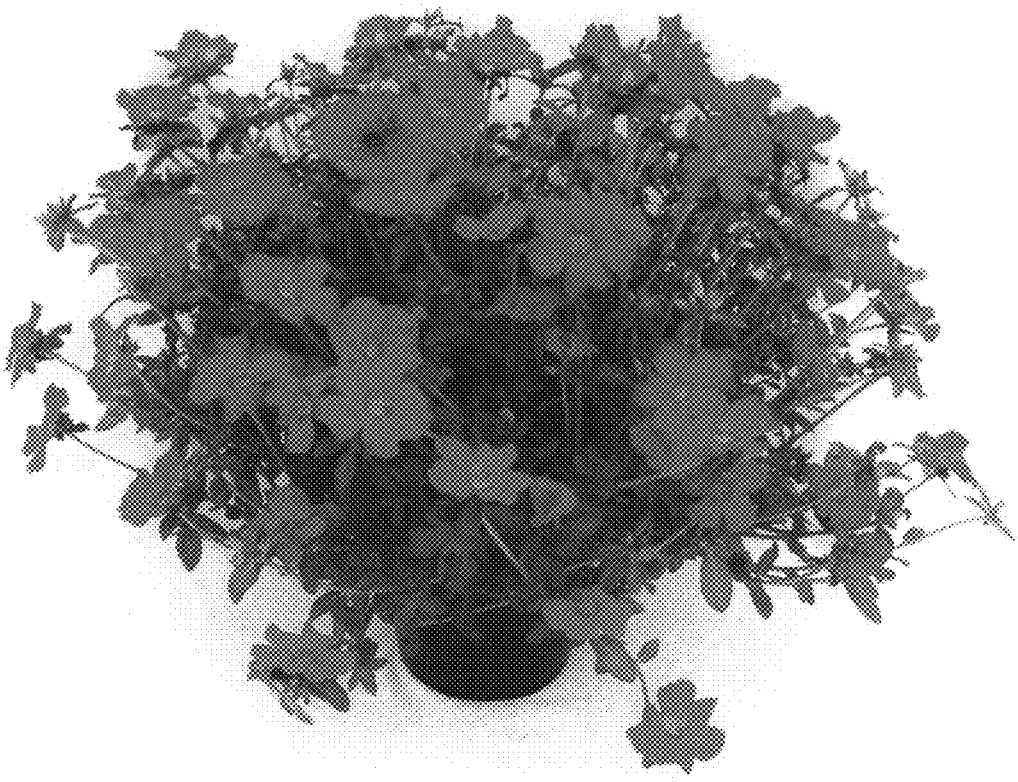
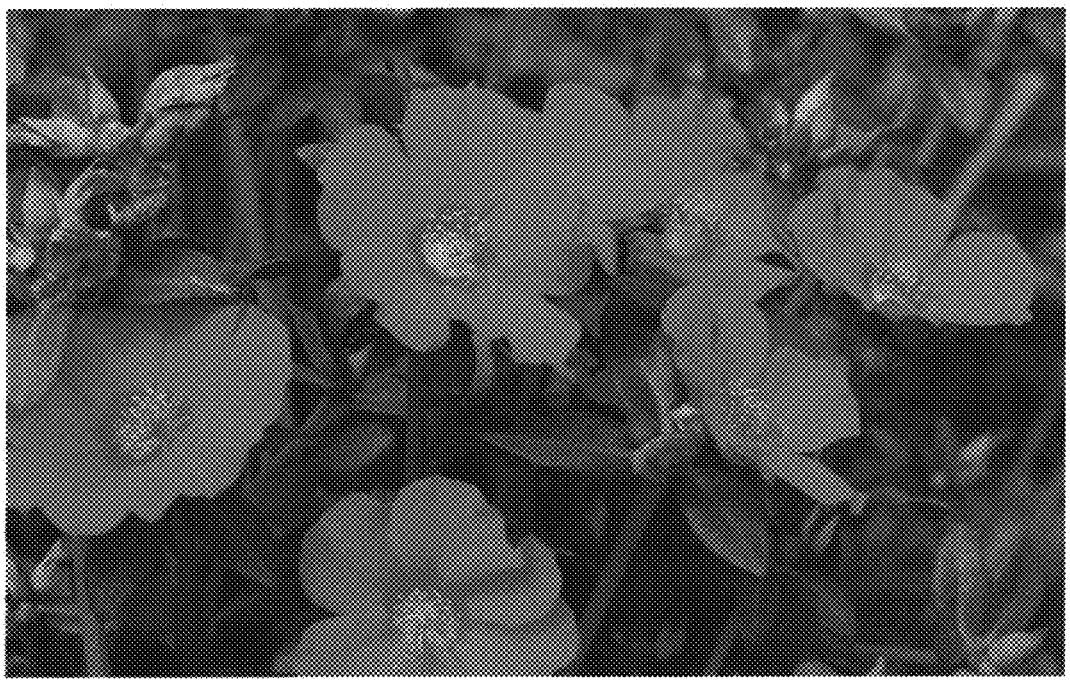

* * * * *